United States Patent
Drevik

(10) Patent No.: US 6,572,599 B2
(45) Date of Patent: Jun. 3, 2003

(54) ABSORBENT ARTICLE WITH IMPROVED LIQUID-HANDLING ABILITY

(75) Inventor: Solgun Drevik, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/967,919

(22) Filed: Oct. 2, 2001

(65) Prior Publication Data

US 2002/0040212 A1 Apr. 4, 2002

Related U.S. Application Data

(60) Provisional application No. 60/236,706, filed on Oct. 2, 2000.

(51) Int. Cl.[7] ............................................. A61F 13/15
(52) U.S. Cl. ......................... 604/385.27; 604/385.24; 604/385.101
(58) Field of Search ................... 604/385.101, 385.24, 604/385.27, 385.23

(56) References Cited

U.S. PATENT DOCUMENTS

| | | | |
|---|---|---|---|
| 5,151,091 A | * 9/1992 | Glaug et al. | .......... 604/385.101 |
| 5,667,609 A | 9/1997 | Liu | |
| 5,827,259 A | 10/1998 | Laux et al. | |
| 6,110,158 A | * 8/2000 | Kielpikowski | ......... 604/385.28 |
| 6,159,190 A | * 12/2000 | Tanaka et al. | ......... 604/385.24 |
| 6,171,290 B1 | * 1/2001 | Boisse et al. | .......... 604/385.01 |
| 6,326,525 B1 | * 12/2001 | Hamajima et al. | .......... 604/378 |

FOREIGN PATENT DOCUMENTS

| | | |
|---|---|---|
| DE | 4422956 | 1/1996 |
| EP | 649644 | 4/1995 |

* cited by examiner

Primary Examiner—John J. Calvert
Assistant Examiner—Angela J Grayson
(74) Attorney, Agent, or Firm—Burns, Doane, Swecker & Mathis, L.L.P.

(57) ABSTRACT

An absorbent article includes an elongate absorbent core having an upper surface and a lower surface, a pair of opposed longitudinal edge portions terminating in longitudinal edges and a pair of opposed transverse edges, the core having a first end portion, a second end portion and a central portion located between the end portions; a liquid permeable topsheet extending over the upper surface; a liquid barrier backsheet covering the lower surface of the absorbent core; barrier strips, each of the barrier strips covering a respective longitudinal edge portion and forming a liquid-retaining pocket along a respective longitudinal edge portion; and a longitudinal elastic member arranged along each of the barrier strips that are placed along each longitudinal edge portion of the absorbent core, the elastic members extending in at least the central portion of the absorbent core; the elastic members each include a plurality of spacers arranged at a distance from each other along a length of the elastic members to create fluid conducting channels.

14 Claims, 3 Drawing Sheets

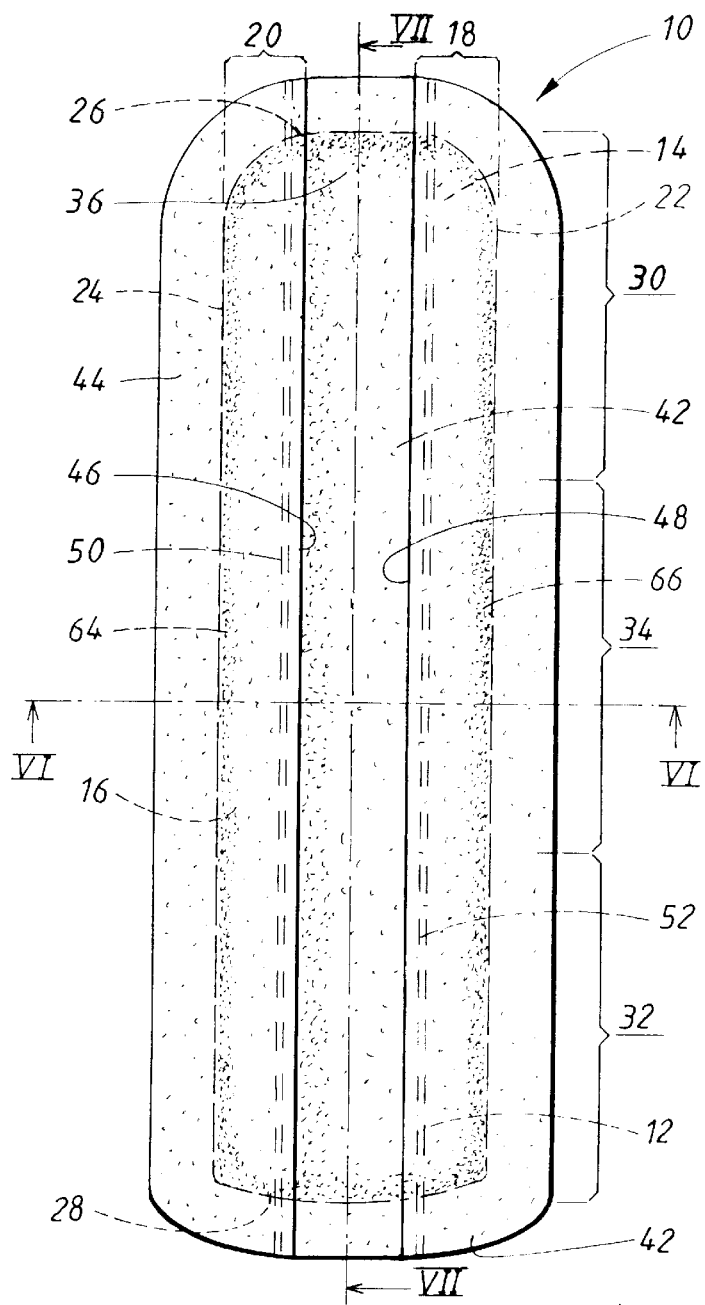
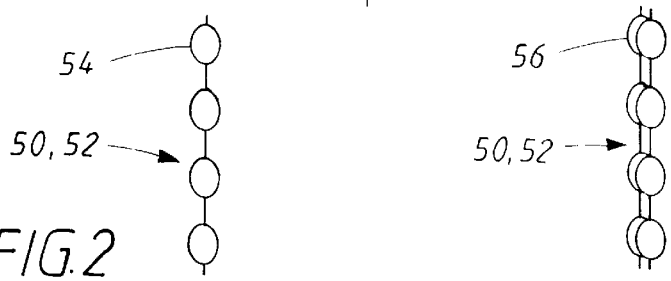
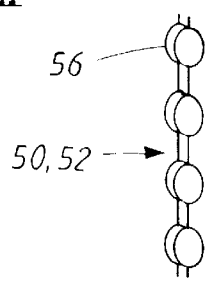
FIG. 1
FIG. 2
FIG. 3

ABSORBENT ARTICLE WITH IMPROVED LIQUID-HANDLING ABILITY

CROSS-REFERENCE TO RELATED APPLICATIONS

The present application claims the benefit of U.S. Provisional Application Serial No. 60/236,706, filed on Oct. 2, 2000, the entire contents of which is hereby incorporated herein by reference.

BACKGROUND OF THE INVENTION

1. Technical Field

The present invention relates to an absorbent article such as a sanitary napkin. The article comprises an elongate absorbent core delimited by an upper surface and a lower surface, a pair of opposed longitudinal edge portions terminating in longitudinal edges, and a pair of opposed transverse edges. The core has a first end portion, a second end portion and a central portion located between the end portions. A liquid permeable topsheet extends over the upper surface, and a liquid barrier backsheet covers the lower surface of the absorbent core. Barrier strips are provided, each strip covering a respective longitudinal edge portion and forming a liquid-retaining pocket along each longitudinal edge portion. A pair of longitudinal elastic members is arranged along the barrier strips that are placed along each longitudinal edge portion of the absorbent core in at least the central portion of the absorbent core.

2. Discussion of Related Art

A common problem associated with an absorbent article such as a diaper or an incontinence pad, which is intended to absorb body fluid, is that fluid leaks out past the side edges of the article. Such leakage is particularly common when gushes of urine are delivered in a short time period and with a high fluid pressure. During urination, the absorbent core cannot instantly absorb all the fluid, which leads to an excessive amount of fluid that flows over the surface of the absorbent article towards the edges not only in the central portion. To help prevent side leakage, it is customary to arrange different types of leakage barriers along the side edges of the article. For example, diapers and incontinence pads are often provided with elastic members which, while the article is being used, are tightened around the user's body and hold the side edges of the article in sealing contact against the body. Elastic members can also be used to form raised edge barriers. It is also possible to create raised barriers in other ways, for example by providing ridges or the like, which prevent liquid from flowing freely over the side edges of the article.

However, it has been found that despite all the efforts, which have hitherto been made to avoid leakage at the side edges, the problem still remains, especially in certain applications. This problem is, for instance, troublesome for bedridden individuals since the risk of leakage increases considerably when the user is lying in a side position. Body fluid which is excreted in this position runs out and gathers, by the effect of gravity, at the longitudinal side edge of the article, where the available absorption material quickly becomes oversaturated with liquid. The remaining liquid that is not absorbed can run freely along the side edge. The risk is of course great that this liquid will be forced out over the side edge of the article and escape if the user moves in such a way that a gap is formed between the article and the user's body.

Conventional hygienic absorbent articles such as sanitary napkins, incontinence pads and the like are provided with an absorbent core which, in theory, is capable of absorbing all the fluid normally discharged by the wearer over an intended exposure time of the article. However, leakage can arise if the absorbent article is not maintained in proper relation with the wearer. One attempt to overcome this problem is to provide a sanitary napkin with so called wings. However, winged sanitary napkins also suffer from certain drawbacks. For example, if a particularly heavy discharge occurs, fluid may spread over the topsheet of the napkin and escape over the wings to thereby stain adjacent clothing. In addition, many wearers regard winged sanitary napkins as being too indiscreet.

Due to their relative narrowness, when sanitary napkins do leak this generally occurs at the side edges. Many attempts have been made to overcome the problem of edge leakage, for example by using strips of resilient material in at least the central portion of the absorbent article which increases the shape stability of the article in the strike zone, i.e. that region of the absorbent article which is first contacted by discharged bodily fluid. In this manner, the risk of bunching of the absorbent article is significantly reduced. In addition, the resilient strips press the longitudinal edges of the absorbent article towards the wearer, thereby causing the article to more readily mould to the body of the wearer. Since the strips need not extend along the entire length of the article, the article may be worn discretely. Advantageously, the remote ends of the strips may serve to impart a bowl-shape to the article to further conform the article to the shape of the wearer.

However, standing gathers is a collective name for these different types of elasticated leakage barriers along the side edges of the article, and they suffer from certain drawbacks. For example, if the standing gathers are subject to an excessive amount of external pressure due to, for example, tight trousers, a soft mattress, when the user is in a vertical position or sitting on a bicycle saddle, the standing gathers will be compressed and thereby somewhat closed, whereby the fluid is prohibited from flowing into the pockets formed by the standing gathers.

OBJECTS AND SUMMARY

While absorbent articles having elasticated side barriers may exhibit improved side edge leakage protection when compared to an absorbent article without elasticated side barriers, a need still exists for an absorbent article which further reduces the risk of side edge leakage while still being sufficiently discrete to satisfy the majority of wearers. It is therefore an object of the present invention to provide an absorbent article that meets these requirements.

The present invention relates to an absorbent article such as a sanitary napkin. The article comprises an elongate absorbent core delimited by an upper surface and a lower surface, a pair of opposed longitudinal edge portions terminating in longitudinal edges, and a pair of opposed transverse edges. The core has a first end portion, a second end portion and a central portion located between the end portions. A liquid permeable topsheet extends over the upper surface, and a liquid barrier backsheet covers the lower surface of the absorbent core. Barrier strips are provided, each strip covering a respective longitudinal edge portion and forming a liquid-retaining pocket along each longitudinal edge portion. A pair of longitudinal elastic members is arranged along the barrier strips that are placed along each longitudinal edge portion of the absorbent core in at least the central portion of the absorbent core.

The above-stated objects are achieved in accordance with the present invention, by the absorbent article being characterised in that the elastic members include spacing means arranged at a distance from each other along the length of the elastic members. The spacing means creates fluid conducting channels that allows fluid to pass under the barrier strips into the pockets, even if the barrier strips are pressed against the top sheet due to an external force, e.g. if the user is sitting or wears tight trousers.

The elastic members may be in different shapes according to different embodiments of the invention. For instance, the elastic members may be in the shape of a string of beads, or in the shape of a string of short cylinders, or in the shape of a string of long cylinders, or there may be a distance material in the form of long cylinders placed within the barrier strips, in a direction from the center of the sanitary napkin to the longitudinal sides of the sanitary napkin.

The elastic members not only serve as means for creating channels, but may also bend the sanitary napkin into a cup-shape preferably at least partially coinciding with the wetting area.

Preferred embodiments will become evident by the subsequent dependent claims.

BRIEF DESCRIPTION OF THE DRAWINGS

The invention will be described in the following by way of example only and with reference to the attached drawings.

FIG. 1 is a plan view of an absorbent article.

FIG. 2 is a schematic view of an elastic member according to the invention.

FIG. 3 is a schematic view of an elastic member according to a second embodiment of the invention.

DETAILED DESCRIPTION OF PREFERRED EMBODIMENTS

Figure 4:
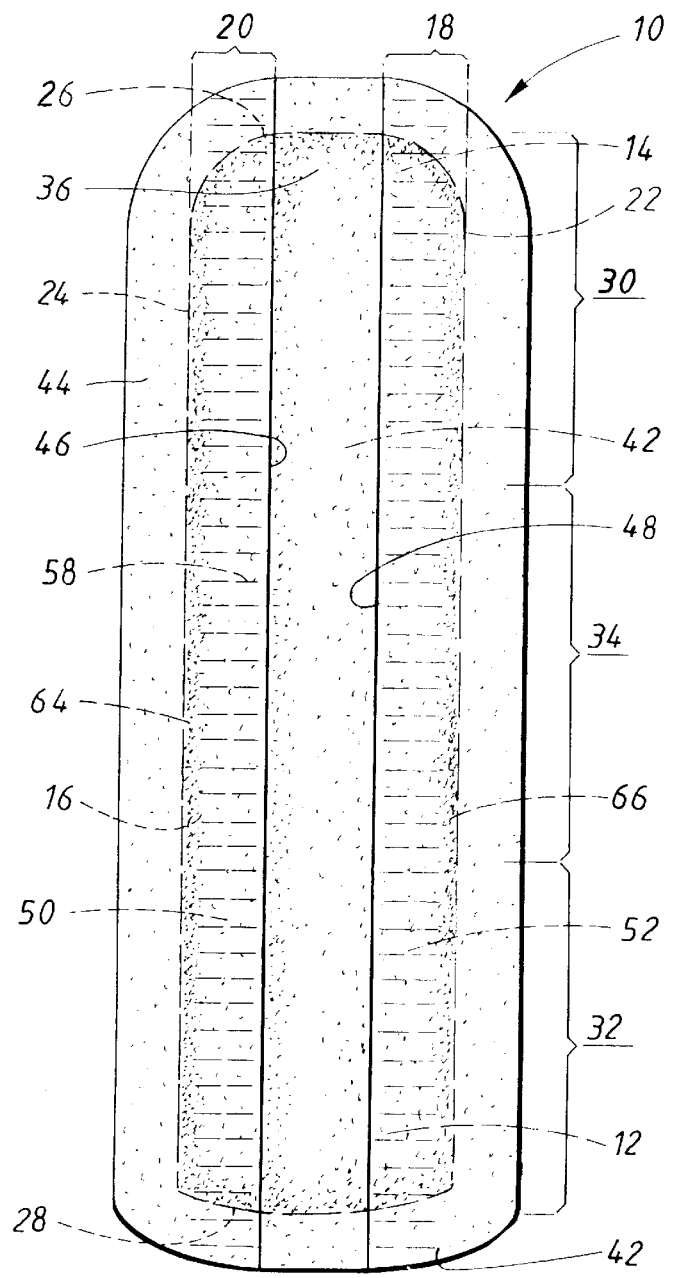
FIG. 4 is a plan view of an absorbent article according to a third embodiment.

In the figures, the reference numbers that recur in the different figures refer to the same feature, and additional features in different embodiments are designated new reference numbers.

As is apparent from FIG. 1, reference numeral 10 generally denotes an absorbent article according to the invention. The absorbent article 10 may be a sanitary napkin having an elongate absorbent core 12 delimited by an upper surface 14 and a lower surface 16, and the core 12 may be any conventional absorbent core. The absorbent core further includes opposed longitudinal edge portions 18, 20 terminating in longitudinal edges 22, 24, and a pair of opposed transverse edges 26, 28. The core is made up of a first end portion 30, a second end portion 32 and central portion 34 located between the end portions. In use, the sanitary napkin is intended to be placed relative the wearer so that the strike zone lies within the central portion 34.

As is typical in the art, the absorbent article 10 is further provided with a liquid permeable topsheet 36 extending over the upper surface 14 of the absorbent core 12. The topsheet 36 may be any conventional topsheet. For example, it may be made from a multi-apertured plastics film, or a non-woven material. The absorbent article may also comprise a liquid barrier backsheet 42 extending over the lower surface 16 of the absorbent core 12. The backsheet 42 may be joined to the topsheet 36 to form a peripheral margin 44 around preferably the entire absorbent core 12. On the backsheet 42, there may be fastening means 68 attached for an increased possibility to fasten the absorbent article to the clothing closest to the wearer's body. The fastening means may be an adhesive, mechanical fastening means such as Velcro or another fastening means suitable for the purpose.

The sanitary napkin 10 further comprises a pair of two longitudinal barrier strips 46, 48, with each strip covering a longitudinal edge portion 18, 20 of the permeable topsheet 36, that forms pockets 64, 66 between the top sheet 36 and the barrier strips 46, 48 along the side edges. The barrier strips 46, 48 may be of either a liquid barrier material or a material that at least resists fluid penetration, e.g., a non-woven hydrophobic fibrous web or another material suitable for the purpose. It is an advantage if the barrier material is breathable, i.e., will permit the passage of air and water vapour. Since the barrier strips 46, 48 may be joined to the peripheral margins 44, the pockets 64, 66 along the edge portions 18, 20 may be seen as enclosed by the barrier strips 46, 48 and the topsheet 36. A pair of pretensioned, longitudinal elastic members 50, 52 are arranged along the barrier strips 46, 48 of the sanitary napkin 10. The elastic members 50, 52 are designed to curve the sanitary napkin 10 to the shape of the user's body and at the same time they constitute means for raising the barrier strips 46, 48 from the upper surface 14 of the sanitary napkin 10. Thus, the elastic members 50, 52 serve to hold the barrier strips 46, 48 of the sanitary napkin 10 in contact against the user's body, in order to ensure that, during use, no gap arises between the sanitary napkin 10 and the user's body, through which gap body fluid could leak from the sanitary napkin 10. Since the material of the barrier strips 46, 48 is primarily hydrophobic, migrating body fluids tend to flow through the absorbent core rather than through the resilient barrier strips 46, 48. Since the barrier strips 46, 48 serve to conceal the longitudinal edge portions 18, 20, any collection of fluid at the edge portions is concealed, thereby imparting an impression of increased safety and cleanliness to the wearer.

Preferably, the elastic members 50, 52 are made of a three dimensional elastic material such as an elastic polymer, elastic non-woven fibrous plastic, elastic foam, silicone, rubber or another material suitable for the purpose.

Figure 6:
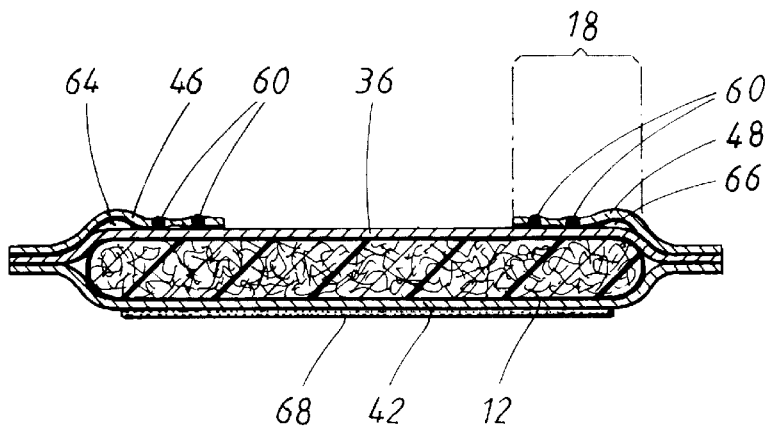
FIG. 6 is a sectional view on a larger scale along line VI—VI of FIG. 1.
Figure 7:
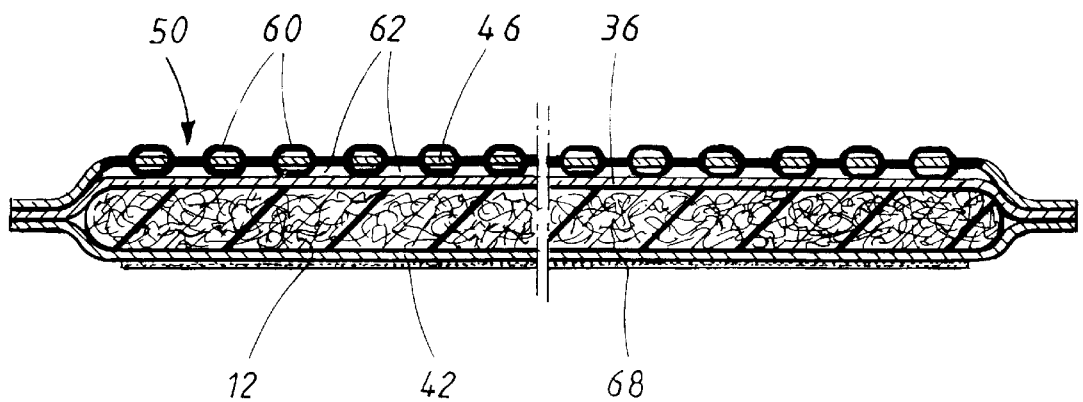
FIG. 7 is a sectional view on a larger scale along line VII—VII of FIG. 1.

In accordance with the present invention, and as best illustrated in FIGS. 2, 6 and 7, the elastic members 50, 52 are in the form of a string of beads 54 as illustrated in FIG. 3. The beads 54 serve as a spacing means 60 (as illustrated in FIGS. 6 and 7) between the barrier strips 46, 48 and the top sheet 36 and will create fluid conducting channels 62 (as illustrated in FIG. 7) between the barrier strips 46, 48 and the top sheet 36 in a direction from the center of the sanitary napkin 10 to the longitudinal sides of the sanitary napkin 10. The channels 62 are especially advantageous when the barrier strips 46, 48 are pressed against the top sheet 36 and the upper surface 14 of the absorbent core 12, by an external force, e.g., tight trousers, or if the user is sitting down. The channels 62 then allow migrating body fluids to flow under the barrier strips 46, 48 even when the barrier strips 46, 48 are pressed against the top sheet 36, thereby increasing the flow through the absorbent core 12 rather than through the barrier strips 46, 48 or over the barrier strips 46, 48. Since the barrier strips 46, 48 serve to cover the longitudinal edge portions 18, 20, and to seal the sanitary napkin 10 against the user's body, any transport of fluid towards the sides of the sanitary napkin is guided via the channels 62 into the pockets 64, 66 which are formed beneath the barrier strips 46, 48 and down through the absorbent core 12, even when the barrier strips 46, 48 are pressed against the top sheet 36, thereby diminishing the risk of side leakage.

The beads 54 may alternatively have other cross-sectional shapes, such as an oval shape. The beads may also have different diameters and/or different cross sections in the same string of beads.

The string of beads 54 according to the present invention, may be created by, for example, point sealing of a three dimensional elastic thread such as an elastic polymer, elastic non-woven fibrous plastic, elastic foam, silicone, rubber or another material suitable for the purpose or two elastic webs with non-elastic spacers between.

In a second embodiment of the invention, and as illustrated in FIGS. 3, 6 and 7, the elastic members 50, 52 are broader than in the first embodiment and they are in the form of a string of short cylinders 56. The short cylinders 56 serve as a spacing means 60 (as illustrated in FIGS. 6 and 7) between the barrier strips 46, 48 and the top sheet 36, and will create channels 62 between the barrier strips 46, 48 and the top sheet 36 in a direction from the center of the sanitary napkin 10 to the longitudinal sides of the sanitary napkin 10, and serves the same purpose as in the first embodiment. Here, short cylinder means a cylinder having a length less than the cylinder diameter. The cylinders may alternatively have other cross-sectional shapes, such as an oval shape. The cylinders may also have different diameters and/or different cross sections in the same string of cylinders.

The string of short cylinders 56 according to the second embodiment of the invention, may be created by, for example, point sealing of a three dimensional elastic thread such as an elastic polymer, elastic non-woven fibrous plastic, elastic foam, silicone, rubber or another material suitable for the purpose or two elastic webs with non-elastic spacers between.

Figure 5:
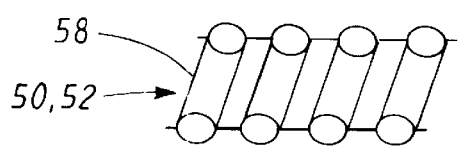
FIG. 5 is a schematic view of an elastic member according to the third embodiment of the invention.

In a third embodiment of the invention, and as illustrated in FIGS. 4, 5 and 7, the elastic members 50, 52 are even broader than in the second embodiment and they are in the form of a string of long cylinders 58. The long cylinders 58 serve as a spacing means 60 (as illustrated in FIG. 7) between the barrier strips 46, 48 and the top sheet 36, and will create channels 62 between the barrier strips 46, 48 and the top sheet 36 in a direction from the center of the sanitary napkin 10 to the longitudinal sides of the sanitary napkin 10, and serves the same purpose as in the second embodiment. Here, long cylinder means a cylinder length longer than the cylinder diameter. The cylinders may alternatively have other cross-sectional shapes, such as an oval shape. The cylinders may also have different diameters and/or different cross sections in the same string of cylinders.

The string of long cylinders 58 according to the third embodiment of the invention, may be created by, for example, point sealing of a three dimensional elastic thread such as an elastic polymer, elastic non-woven fibrous plastic, elastic foam, silicone, rubber or another material suitable for the purpose or two elastic webs with non-elastic spacers between.

In a fourth embodiment of the invention, not shown in the figures even though FIGS. 4, 5 and 7 illustrate the fourth embodiment schematically, the string of long cylinders 58 according to the third embodiment of the invention may be substituted by a distance material in the form of long cylinders (not shown) and elastic members, e.g., the elastic members 50, 52 previously mentioned. The cylindrical distance material is placed within the barrier strips 46, 48 or in a manner suitable for the purpose of using the distance material to create channels 62 between the barrier strips 46, 48 and the top sheet 36 in a direction from the center of the sanitary napkin 10 to the longitudinal sides of the sanitary napkin 10. The elastic members 50, 52 may be a pair of pretensioned, longitudinal elastic members 50, 52 that are arranged along the barrier strips 46, 48 of the sanitary napkin 10. The elastic members 50, 52 are designed to curve the sanitary napkin 10 to the shape of the user's body and at the same time they constitute means for keeping open the side pockets 64, 66 created beneath the barrier strips 46, 48 and the sanitary napkin 10.

The distance material in the form of long cylinders according to the fourth embodiment of the invention may alternatively have other cross-sectional shapes, such as an oval shape. The distance material may also have different diameters and/or different cross sections in the barrier strips 46, 48.

The long cylinders according to the fourth embodiment of the invention, may be a three dimensional elastic thread such as an elastic polymer, elastic non-woven fibrous plastic, elastic foam, silicone, rubber or another material suitable for the purpose or two elastic webs with non-elastic spacers between.

The short and the long cylinders may be up to 50 mm long.

For ease of manufacturing and to ensure that the risk of edge leakage anywhere along the length of the absorbent article is minimal, the barrier strips 46, 48 and thus, the liquid-retaining pockets 64, 66 preferably extend along the entire length of the absorbent core. However, since the shape stability of the absorbent article is most critical only in the central portion 34 of the absorbent core, the barrier strips 46, 48 and the elastic members 50, 52 need only occupy the central portion, which often is the case in the use of sanitary napkins or panty liners. However, if desired, the barrier strips 46, 48 and the elastic members 50, 52 may extend into the first and second end portions 30, 32, which often is the case in the use of incontinent articles or diapers, where it is possible to tighten the sides of the absorbent article around the body of the user, which normally is not the case in the use of sanitary napkins or panty liners. Further incontinent articles and diapers are subject to a larger amount of fluid during rather high pressure when the user urinates, compared to the smaller sanitary napkins and panty liners which normally are not used for incontinent protection. During urination, the absorbent core 12 cannot instantly absorb all the fluid, which leads to an excessive amount of fluid that spreads over the surface of the absorbent article towards the edges not only in the central portion 34. This increases the need to have a sufficient edge leakage protection such as the barrier strips 46, 48 and thus, the liquid-retaining pockets 64, 66, preferably extending along the entire length of the absorbent core.

The absorbent article according to any one of the preceding embodiments is characterized in that the thickness of the spacing means 60 is preferably at least 1 mm, and that the thickness of the spacing means 60 defines the maximum height of the channel. The thickness of the spacing means also means the diameter when the spacing means are cylindrical or spherical.

Preferably, the central portion 34 of the absorbent core 12 comprises between 20% and 60%, preferably between 30 and 45%, and most preferably about one third, of the length of the absorbent core.

Obviously, the substantially hydrophobic barrier strips 46, 48 and the elastic members 50, 52 may not extend over the entire width of the absorbent core since this would prevent passage of body fluids into the absorbent core 12. Accordingly, each side edge 46, 48 and elastic member 50, 52 has an extension transversely across the absorbent core, with the extension being between 5% and 25% of the total width of the sanitary napkin at the wetting area.

The distance between the spacing means 60, i.e., the width of the channel, is 1–20 mm.

The invention is not restricted to the embodiments described above and shown in the drawings, but may be modified within the scope of the appended claims. For example, the absorbent article may be a sanitary napkin, a diaper, an incontinent protection article, a panty liner or any absorbent article suitable for the purpose. The absorbent article is not restricted to any shape or configuration, but may be of any shape suitable for the purpose, e.g., triangular, hour-glass shaped or rectangular. Also, the elastic members and the distance material may be of a stiff material, i.e., the side barriers with the distance material will still create the channels for transporting the fluids. The sanitary napkin may also be equipped with wings.

At least the longitudinal edge portion 18, 20 of the absorbent article may be made profiled and may include spacing means arranged at a distance from each other along the length of the longitudinal edge portion 18, 20 to create fluid conducting channels. The longitudinal edge portion 18, 20 may be made profiled by a groove compression of the topsheet 36 or by a groove compression of a suitable part of the absorbent core 12. The groove compression compresses the material in certain parts with a certain distance between the compressed parts, and the spacing means consists of the uncompressed parts. The longitudinal edge portion 18, 20 may also be made profiled by inserting a distance material in the topsheet 36 or in the absorbent core. The profiling of the absorbing article is not limited to the longitudinal edge portion 18, 20, but the whole upper surface may be profiled by any of the above described techniques.

What is claimed is:

1. An absorbent article, comprising:
   an elongate absorbent core having an upper surface and a lower surface, a pair of opposed longitudinal edge portions terminating in longitudinal edges and a pair of opposed transverse edges, the core having a first end portion, a second end portion and a central portion located between the end portions;
   a liquid permeable topsheet extending over the upper surface;
   a liquid barrier backsheet covering the lower surface of the absorbent core;
   barrier strips, each of the barrier strips covering a respective longitudinal edge portion and forming a liquid-retaining pocket along a respective longitudinal edge portion; and
   a longitudinal elastic member arranged along each of the barrier strips that are placed along each longitudinal edge portion of the absorbent core, the elastic members extending in at least the central portion of the absorbent core;
   the elastic members each include a plurality of spacers arranged at a distance from each other along a length of the elastic members to create fluid conducting channels.

2. The absorbent article according to claim 1, wherein the elastic members are in a shape of a string of beads and the spacers comprise the beads.

3. The absorbent article according to claim 1, wherein the elastic members are in a shape of a string of cylinders having a length less than a cylinder diameter and the spacers comprise the cylinders.

4. The absorbent article according to claim 1, wherein the elastic members are in a shape of a string of cylinders having a length longer than the cylinder diameter, and that the spacers comprise the cylinders.

5. The absorbent article according to claim 1, wherein the spacers are a distance material in the form of cylinders placed within the barrier strips in a direction from a center of the sanitary napkin to the longitudinal edges of the absorbent article.

6. The absorbent article according to claim 1, wherein the barrier strips are primarily hydrophobic.

7. The absorbent article according to claim 1, wherein the elastic members are a three dimensional non-woven fibrous plastic wadding or a foamed plastic.

8. The absorbent article according to claim 1, wherein the pockets extend along an entire length of the absorbent core.

9. The absorbent article according to claim 1, wherein the pockets extend along only the central portion of the absorbent core.

10. The absorbent article according to claim 1, wherein the central portion of the absorbent core comprises between 20% and 60% of the absorbent core.

11. The absorbent article according to claim 1, wherein the central portion of the absorbent core comprises between 30 and 45% of the length of the absorbent core.

12. The absorbent article according to claim 1, wherein the central portion of the absorbent core comprises about one third of the length of the absorbent core.

13. The absorbent article according to claim 1, wherein the barrier strips have an extension transversely across the absorbent core, the extension being between 5% and 25% of the total width of the sanitary napkin at a wetting area.

14. The absorbent article according to claim 1, wherein a thickness of the spacers is at least 1 mm.

* * * * *